United States Patent [19]

DeLoach et al.

[11] 4,389,209

[45] Jun. 21, 1983

[54] METHOD OF PROVIDING SYSTEMIC PROTECTION FROM BLOODSUCKING INSECTS AND OTHER PARASITES USING ENCAPSULATED ADDITIVES IN RESEALED ERYTHROCYTES

[75] Inventors: John R. DeLoach; Robert L. Harris; Mayery Richard T., all of Bryan; Garret M. Ihler, College Station, all of Tex.

[73] Assignee: The United States of America as represented by the Secretary of Agriculture, Washington, D.C.

[21] Appl. No.: 332,905

[22] Filed: Dec. 21, 1981

Related U.S. Application Data

[62] Division of Ser. No. 160,753, Jun. 18, 1980, Pat. No. 4,327,710.

[51] Int. Cl.³ ............................................. A61M 5/00
[52] U.S. Cl. ..................................... 604/53; 128/1 R
[58] Field of Search .............. 128/1 R, 213 R, 213 A, 128/214 R, 260; 604/51–53

[56] References Cited

PUBLICATIONS

"Enzyme Loading of Erythrocytes", *Proc. Nat. Acad. Sci.*, vol. 70, No. 9, Ihler et al.
"Release and Uptake of Hemoglobin and Ions in Red Blood Cells Induced by Dielectric Breakdown", *Biochemica et Biophysica Acta*, 394, (1975).
"A Dialysis Procedure for Loading Erythrocytes with Enzymes and Lipids", *Biochemica et Biophysica Acta*, 496, (1977), DeLoach et al.
"An Erythrocyte Encapsulation Dialyzer", *Analytical Biochem.*, 102, 220–227, (4–1980).

*Primary Examiner*—Richard J. Apley
*Assistant Examiner*—T. J. Wallen
*Attorney, Agent, or Firm*—M. Howard Silverstein; David G. McConnell; Raymond C. VonBodungen

[57] ABSTRACT

A process for encapsulating additives in resealed erythrocytes from the blood of certain mammals. The invention provides a method of preparing material in substantial quantities, to be employed as vaccine which, when reinjected into these mammals, provides a systemic protection against bloodsucking insects or other parasites.

1 Claim, 2 Drawing Figures ated by FIG. 1 is as one designed specifically for a volume of about 13 liters. The thermostat 8 used in the particular configuration was a Ranco Type Thermostat.

METHOD OF PROVIDING SYSTEMIC PROTECTION FROM BLOODSUCKING INSECTS AND OTHER PARASITES USING ENCAPSULATED ADDITIVES IN RESEALED ERYTHROCYTES

CROSS REFERENCE TO RELATED APPLICATIONS

This invention is a division of Ser. No. 160,753, filed June 18, 1980, now U.S. Pat. No. 4,327,710.

BACKGROUND OF THE INVENTION (1) Field of the Invention

This invention relates to an apparatus for preparing large quantities of vaccine for mammals, and to the process for employing the substantially evacuated red blood cells of said mammals, thus providing a means of utilizing the erythrocytes in the vaccination of these animals.

(2) Description of the Prior Art

G. M. Ihler, et al. in *Proceedings of the National Academy of Science of the U.S.A.*, Volume 70, pp. 2663–2666 (1973), used a large hypotonic dilution to encapsulate enzymes with a maximum encapsulation less than 1%. Later a one-third to one-fifth hypotonic dilution was used to encapsulate the enzyme uricase. In 1976 and 1977 other variations on the hypotonic dilution method have been used for other animal erythrocytes (see E. Ang, et al., *Experimental Cell Research*, Volume 104, pp. 430–434). Another method of encapsulation of substances in erythrocytes employs electrochemical shock [see F. Riemann, et al., *Biochimica et Biophysica Acta*, Volume 394, pp. 449–462 (1975)]; however, this method requires sophisticated equipment to generate exponentially decaying electric fields.

J. R. DeLoach et al. reported in 1977 a dialysis method for encapsulating enzymes and lipids in erythrocytes, where up to 45% of the added substances could be encapsulated. In that procedure, human erythrocytes at 70% to 80% hematocrit were dialyzed against 1 to 2 liters of distilled water for 2 hours. At 5 to 10 minute intervals the dialysis bag was removed and its contents mixed. Sufficient homogenous mixing was not achieved and it was difficult to prepare large quantities of resealed erythrocytes.

The prior art also discloses the use of dialysis to encapsulate enzymes with a maximum of about 30% encapsulated (see G. L. Dale, et al., *Biochemical Medicine*, Volume 18, pp. 220–225, 1977). More recently, M. Yaiuzimi, et al., in *Cell*, Volume 15, p. 245 (1978) employed a dialysis procedure for encapsulation of Immunoglobulin G (IgG) in erythrocyte ghosts. Although these authors reported the IgG concentrations inside the erythrocyte ghosts, no report on percent uptake was made.

The reports of the prior art indicate that there is yet much to be done to advance the state of the art. The present invention provides a step in that direction.

DEFINITIONS APPLICABLE TO THIS INVENTION

Resealed erythrocytes—These are red blood cells that have been swelled to the extent that pores open in their membrane, then are restored to isotonic condition and annealed. They are unlike white ghosts in that they retain about from 50% to 70% of their soluble cellular components.

Erythrocyte ghosts—This term is sometimes employed as synonymous with resealed erythrocytes.

Isotonic—This term is used to describe a solution whose osmotic pressure is about the same as normal mammalian blood.

Hypertonic—This term is used to describe a solution whose osmotic pressure is less than osmotic pressure of mammalian blood.

Osmolality—The molality of an ideal solution that exerts the same osmotic pressure as the solution being considered.

Additive—Any substance which may be combined with erythrocytes for the purpose of encapsulation.

Exogenous substance—This term is employed synonymous with additive.

SUMMARY OF THE INVENTION

The present invention provides an apparatus and a process designed specifically for encapsulating certain chemical substances, thus providing a means of dispersing said substances via the circulatory system of certain live animals. The apparatus of the present invention provides a means of utilizing resealed erythrocytes as carriers of the chemicals. The apparatus though controlled dislysis causes a swelling of the erythrocyte until pores appear in the erythrocyte membrane, allowing equilibration of intra- and extracellular content, and finally resealing of the cell once it has been filled with preferred additives. In this manner the carrier erythrocytes can be placed back into the live circulatory system of a host animal, therein to disperse its contents at the predetermined time.

The main object of the present invention is to provide an efficient apparatus and method of preparation of relatively large quantities of encapsulated erythrocytes to convey and disperse via the circulatory system of a host animal such chemicals as, for example pesticides, enzymes, and the like, to be released at precisely calculated times, in precisely calculated quantities, for investigative and other purposes.

DESCRIPTION OF THE PREFERRED EMBODIMENTS

Figure 1:
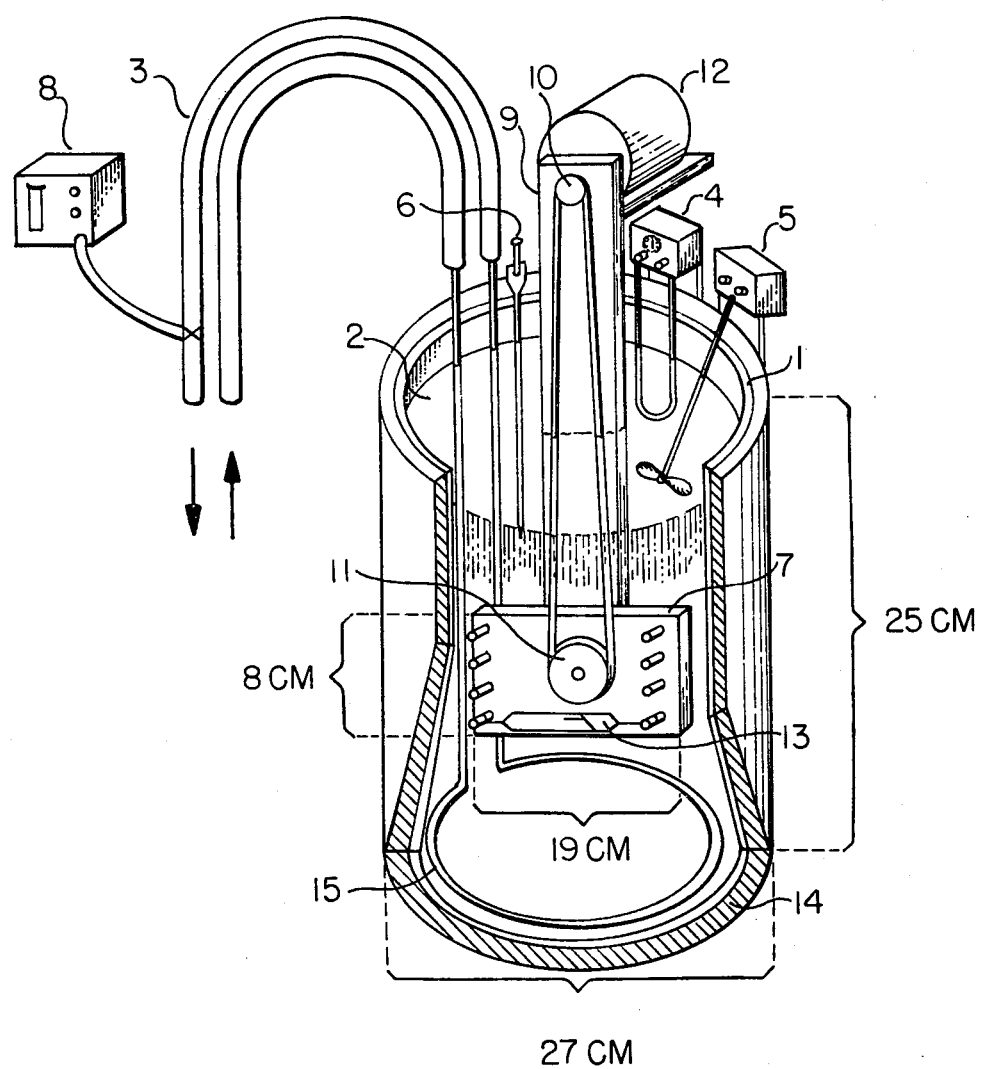
FIG. 1 is a perspective view of the Dialyzing Apparatus of the present invention.

FIG. 1 is provided to illustrate the basic configuration of the Dialyzing Apparatus of the present invention. The particular illustration pertains to a working model which has served well in the investigative work of the present invention. Modification of this configuration can be employed without disturbing the basic design, if needed.

FIG. 1 shows a design consisting of a dialyzer container 1, a dialyzing solution 2, which in the sequence required to perform its task, generally, is changed to contain two different solutions, at different times; a cooling means 3, a heating means 4, an aggitating means 5, a heat-registering device 6, a specimen rotating means 7, and a thermostat 8.

The configuration of the Dialyzing Apparatus illustrated by FIG. 1 is as one designed specifically for a volume of about 13 liters. The thermostat 8 used in the particular configuration was a Ranco Type Thermostat.

It served well in controlling the chilled water flow at between 26° and 4.5°, as needed. The heater 4 was a 400 watt heater. A temperature homogeniety was maintained by the aggitating means 5, which provided a stirring by the rotation of the shaft and propeller at from 500 to 5000 rpm. Of particular interest is the specimen rotating means 7. This consists of a pulley assembly 9. The pulley assembly consists of a vertical member and a pulley at each end. There is an upper pulley 10 which responds to the force of rotation provided by an electric motor 12 through a shaft. In this configuration a 10 rpm electric motor provided the suitable energy (a 1/100 HP Gearmotor) needed.

Lower pulley 11, located in the pulley assembly about 32 cm directly below upper pulley 10, is energized by a belt which drives these pulleys. Rotating means 7 is secured to lower pulley 11, and is a specimen holder which in this configuration holds 10 specimens, each containing about 20 ml of erythrocytes. FIG. 1 shows a single specimen 13 in place. The specimen 13 consists of dialysis tubing sealed at one end and attached to a 3-way Leuer lock valve (secured by a rubber band in this instance). This arrangement provides easy access to the specimen 13 contents.

In the particular apparatus shown in FIG. 1 the large vessel was 25 cm in height, and 27 cm in width. This width was an outside diameter measurement. The inside diameter of this particular dialyzer vessel was 19 cm. Insulation is provided in this particular configuration by providing space 14 as an insulation means. However, it may in some instances be more convenient to provide less space and a layer of styrofoam. A cooling means 3 carries chilled water to the bottom of the dialyzer vellel 1. This task is performed by a cooling coil 15 at the bottom of the vessel.

The cooling of the dialyzer vessel (or reservoir) was accomplished by circulating a 50% ethylene glycol-water mixture via a stainless steel cooling coil. The thermostat 6 which controlled the coolant flow was attached to the exit side of the cooling coil 15. Typically a temperature of 0.5° C. could be maintained with relative ease. The alternate, a higher temperature of up to 45° C. was achieved by a 500 watt immersion heater. The dialysis of the investigative work of this invention was the dialysis of erythrocytes at the temperature range of about from 0.5° to 4.0° C.

An essential feature of the dialyzer of the present invention is the rotation of the dialysis tubing in a vertical plane. The erythrocytes do not mix well at a rotation speed greater than 15 rpm. The preferred rotation speed at the preferred temperatures was about 5 rpm. Attention is called to the fact that the dialysis tubing should be inflated with air and should contain no more than about 75% of its volume in blood for sufficient mixing.

By dialyzing against a large volume—for the intents and purposes of this invention 11 liters was most common—reduction in the somolality of the contents of the dialysis tubing can be achieved in a short period of time. In the investigative work which yielded the data presented in FIG. 2 the exit of small molecules and ions from the bag was measured. The osmolality of the dialysis medium was 38 mOsm. In this work the osmolality of the contents of the dialysis bag reached 70 in 1 hour. The exit of $^{14}C$-sucrose from the bag had a similar rate. As seen in the data presented in FIG. 2, the exit of the molecules during the first hour follows first-order kinetics. The equation (1) can be used to calculate the dialysis time required to reach certain osmolality.

$$C = C_o e^{-Kt} \qquad \text{EQUATION (1)}$$

C = concentration at some time up to 60 min.
$C_o$ = initial concentration
K = rate constant, $-2.84 \times 10^{-2}$ min$^{-1}$
t = time of dialysis 0 to 60 min For example, to reach osmolality of 200 mOsm/kg from initial osmolality of 330 mOsm/kg would require 18 min.

$$t = 2.303/K(\log C_o/C)$$

$$t = 2.303 \times 10^{-2} \text{ min}^{-1}(\log 330 - \log 200)$$

$$t = 18 \text{ min}$$

Figure 2:
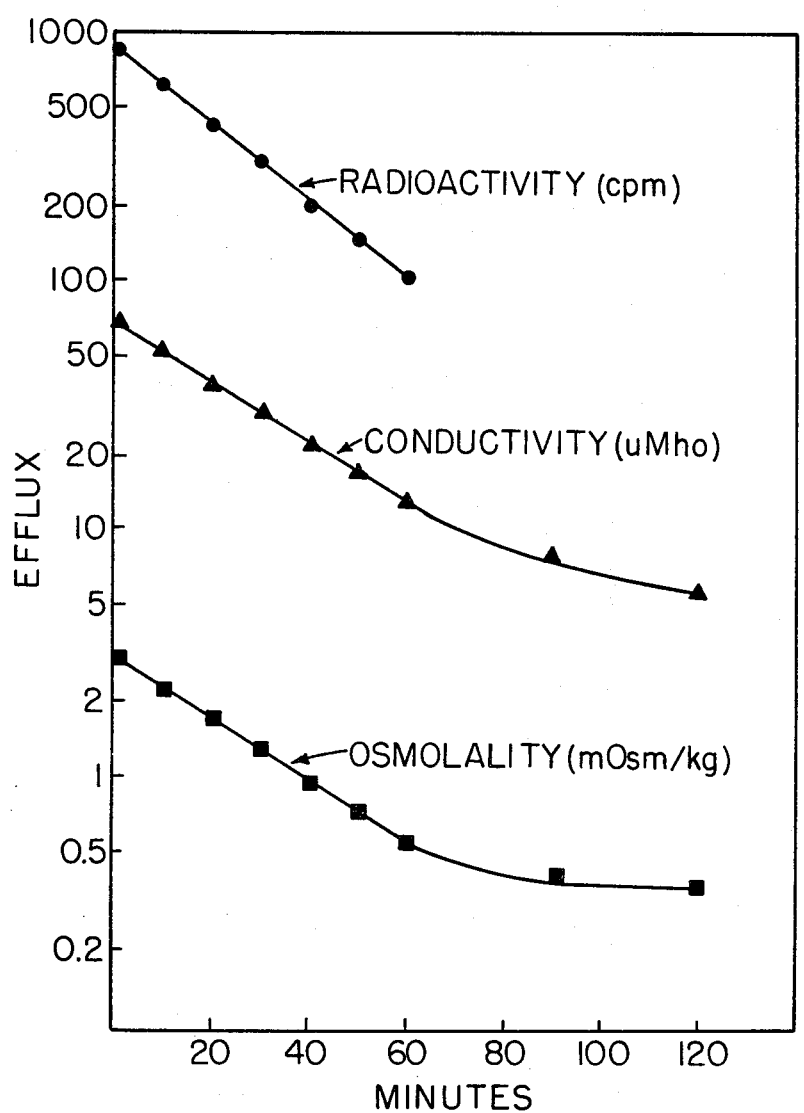
FIG. 2 is a composite graph, which provides a comparative study of the efflux from the dialysis tubing of the invention.

This example calculation is supported by the data in FIG. 2.

The following examples are provided to illustrate preferred embodiments of the present invention and should not be construed as limiting the invention in any manner whatever.

EXAMPLE 1

Freshly drawn heparanized bovine, equine and porcine blood was washed five times in 5 volumes of phosphate buffer pH 7.0, containing 15 mM NaHPO$_4$, 2 mM mgCl$_2$, 2 mM glucose, 144 mM NaCl. Ten ml of washed packed erythrocytes (70-80% hematocrit) were placed in dialysis membrane 13 and the remaining volume was filled with air before it was attached to the specimen holder 7. Initially dislysis was done at 4° C. At varying intervals small aliquots were removed from the dialysis tubing and the additive was mixed with these for 30 minutes at 24° to 26° C. Isotonic conditions were restored by adding sufficient 9% NaCl or, after mixing with the additive to be encapsulated, tonicity was restored by continuing dialysis against an isotonic solution. The optimum dialysis time was determined from the % of additive encapsulated. This data is summarized in Table 1.

Equine whole blood and washed equine erythrocyte had a tendency to aggultinate at temperatures below 22° C. Dialysis of equine erythrocytes was done at 4° increments from 1° to 37° and it was determined that 24° was the optimum dialysis temperatures. The data presented in Table 1 is a summary of the encapsulation of the additives.

TABLE 1

| | Encapsulation of β-Galactosidase, Alkaline Phosphatase, and $^{14}C$-Sucrose by Animal and Human Erythrocytes | | | |
|---|---|---|---|---|
| Erythrocytes | Amount added | Amount recovered in erythrocytes | % recovered in erythrocytes | % recovery of ghosts |
| 1. Equine | | | | |
| β-Galactosidase | | | | |
| (μmoles/min) | 0.76 | 0.20 | 25.9 | 52.0 |
| Alkaline phosphatase | | | | |
| (μmoles/min) | 4.1 | 1.3 | 31.7 | |

TABLE 1-continued

Encapsulation of β-Galactosidase, Alkaline Phosphatase, and $^{14}$C-Sucrose by Animal and Human Erythrocytes

| Erythrocytes | Amount added | Amount recovered in erythrocytes | % recovered in erythrocytes | % recovery of ghosts |
|---|---|---|---|---|
| Sucrose (cpm) | $4.4 \times 10^5$ | $1.29 \times 10^5$ | 29.3 | |
| 2. Bovine | | | | |
| β-Galactosidase (μmoles/min) | 0.14 | 0.04 | 26.8 | 60.0 |
| Alkaline phosphatase (μmoles/min) | 3.75 | 1.0 | 26.7 | |
| Sucrose (cpm) | $4.26 \times 10^5$ | $1.28 \times 10^5$ | 30.0 | |
| 3. Porcine | | | | |
| β-Galactosidase (μmoles/min) | 0.77 | 0.20 | 26.5 | 52.0 |
| Alkaline phosphatase (μmoles/min) | 3.8 | 1.1 | 28.9 | |
| Sucrose (cpm) | $4.40 \times 10^5$ | $1.24 \times 10^5$ | 28.2 | |
| 4. Human | | | | |
| β-Galactosidase (μmoles/min) | 0.76 | 0.30 | 39.1 | 68.0 |
| Alkaline phosphatase (μmoles/min) | 4.1 | 1.6 | 39.0 | |
| Sucrose (cpm) | $4.4 \times 10^5$ | $1.54 \times 10^5$ | 35.0 | |

Ten ml of washed packed erythrocytes were dialyzed for 25 to 30 min against 11 liters of buffer at 1 to 2° C. except that dialysis of equine erythrocytes was done at 24° C. In separate experiments, β-galactosidase, alkaline phosphatase and $^{14}$C-sucrose were added to the dialyzed erythrocytes, which were then mixed, annealed and washed. Percent recovery of ghosts was calculated from the total number of ghosts recovered divided by the total number added times 100. Percent recovered in ghosts was calculated from the amount encapsulated divided by the amount added times 100. The dialysis membrane used was one which retains molecules of a molecular weight ca. 12,000 to 14,000 or greater.

EXAMPLE 2

Two hundred ml of washed packed bovine erythrocytes were introduced into 10 specimen containers 7 and dialyzed for 40 min, were mixed with $55.8 \times 10^7$ DPM of $^{14}$C sucrose for 30 min, were restored to isotonic condition, were annealed at 37° C. for 30 min, and were washed four times with 10 volumes of buffer. The data is summarized in Table 2. Clearly, % encapsulation was reasonably high and due in part to the high % recovery of resealed erythrocytes. This data demonstrates that 200 ml of resealed erythrocytes can be prepared with the dialysis apparatus.

TABLE 2

| | |
|---|---|
| Volume of Erythrocytes | 200 ml |
| Dialysis Times | 40 min |
| % Additive Encapsulated | 37.3% |
| % Recovery of Resealed Erythrocytes | 67% |

The significance of dialysis time is presented in Table 3. Ten ml of bovine erythrocytes were dialyzed in a 15 ml dialysis bag and at 10 min intervals aliquots were removed, additive consisting of 0.67 units enzyme was mixed, tonicity was restored and the resealed erythrocytes were annealed. The optimum dialysis time was 20 to 30 min and further dialysis reduces the % of additive encapsulated. This example is not limited to bovine and is typical for each animal.

TABLE 3

Time Course for Encapsulation of β-Galactosidase by Bovine Erythrocytes

| Time (min) | % of total enzyme encapsulated | % of total erythrocytes recovered | Osmolality (milliosmos/kg) | Volume of erythrocyte (nl) |
|---|---|---|---|---|
| 0 | 0 | 96 | 324 | 40 |
| 10 | 12 | 54 | 228 | 56 |
| 20 | 30 | 56 | 180 | 60 |
| 30 | 28 | 53 | 130 | 60 |
| 40 | 27 | 50 | 81 | 61 |
| 50 | 24 | 40 | 51 | 60 |
| 60 | 22 | 36 | 41 | 60 |

Ten ml of erythrocytes were placed in a 15 ml dialysis bag and dialyzed against 11 liters of buffer. At the times indicated 0.2 ml aliquots were removed and mixed with 0.67 units of β-galactosidase. Percent enzyme encapsulated was calculated from the amount encapsulated divided by the amount added times 100.

The significance of annealing temperature was examined and is reported in Table 4. Resealed bovine erythrocytes previously mixed with additive consisting of $^{14}$C-sucrose were incubated at varying temperatures from 1° to 41° C. It was determined that annealing of 37° to 41° C. is optimal for bovine erythrocytes. This example is not limited to bovine and is typical for each animal.

TABLE 4

Effect of Annealing Temperature on Encapsulation of $^{14}$C-Sucrose in Bovine Erythrocyte Ghosts and on Percent Recovery of Ghosts

| TEMPERATURE (°) | % ENCAPSULATED | % RECOVERY OF ERYTHROCYTE GHOSTS |
|---|---|---|
| 1 | 14.0 | 30.0 |
| 15 | 17.0 | 37.0 |
| 20 | 21.0 | 45.0 |
| 25 | 23.0 | 49.0 |
| 30 | 23.9 | 50.0 |
| 37 | 31.1 | 58.0 |
| 39 | 28.9 | 57.0 |
| 41 | 30.5 | 38.0 |

One ml aliquots of $^{14}$C-sucrose-loaded erythrocytes were annealed in $12 \times 75$ mm culture tubes at the indicated temperature followed by extensive washing and restoration to a volume of 1 ml. Percent encapsulation was determined as described in Table 2. Percent recovery of erythrocyte ghosts was determined from cell counts made with a Coulter counter.

We claim:

1. A method of treating animals to provide systemic protection against blood sucking parasites comprising:
   (a) withdrawing whole blood from a live animal;
   (b) preparing washed packed erythrocytes from said whole blood;
   (c) encapsulating within said erythrocytes an effective amount of a blood sucking parasite controlling material;
   (d) recovering the erythrocytes containing said material;
   (e) injecting said live animals with the recovered erythrocytes.

* * * * *